United States Patent [19]

Levine et al.

[11] 4,381,665

[45] May 3, 1983

[54] METHOD FOR DETERMINING SATURATION CHARACTERISTICS OF A POROUS MATERIAL

[75] Inventors: Joel L. Levine, Garland; Benjamin F. Marek, Dallas, both of Tex.

[73] Assignee: Mobil Oil Corporation, New York, N.Y.

[21] Appl. No.: 281,451

[22] Filed: Jul. 8, 1981

[51] Int. Cl.³ ............................................. G01N 5/02
[52] U.S. Cl. ........................................... 73/73; 73/153
[58] Field of Search .............................. 73/73, 38, 153

[56] References Cited

U.S. PATENT DOCUMENTS 2,345,935  4/1944  Hassler ................................. 73/38
2,867,116  1/1959  Aronofsky et al. ................... 73/38
3,018,660  1/1962  Schmid ............................... 73/38 X Primary Examiner—Jerry W. Myracle
Attorney, Agent, or Firm—Charles A. Huggett; Michael G. Gilman; George W. Hager

[57] ABSTRACT

A method for determining the fluid saturation conditions of a porous material containing a liquid hydrocarbon. An insoluble displacing liquid is pumped into such porous material and displaces the liquid hydrocarbon. The amount of displaced liquid hydrocarbon is monitored as a measure of the saturation condition of the porous material at any given time.

5 Claims, 4 Drawing Figures

METHOD FOR DETERMINING SATURATION CHARACTERISTICS OF A POROUS MATERIAL

BACKGROUND OF THE INVENTION

This invention relates to the measurement of saturation characteristics of porous materials with respect to fluids and more particularly to the measurement of the oil/water saturation characteristics of porous materials such as core samples from hydrocarbon bearing subterranean formations.

In many instances it is desirable to know the saturation characteristics of an earth material forming the matrix of a subterranean hydrocarbon reservoir in order to estimate the potential total production or the rate of production of hydrocarbons from the reservoir. Saturation may be defined as the tendency of the porous material to retain one fluid phase with which it is impregnated upon passage therethrough of one or more other fluid phases.

To attach significance to the measurement of such characteristics of porous materials, it is necessary to known the quantity of each fluid phase in the material, or the extent of saturation of the porous material with respect to each fluid phase, when equilibrium, under the procedures for measurement, have been established or to known the variation in the extent of saturation before or after establishment of equilibrium.

SUMMARY OF THE INVENTION

The present invention, is directed to a method for determining the saturation characteristics of a porous material from a subterranean formation. A closed fluid system of a multiphase fluid is established with one phase being a liquid hydrocarbon and another phase being an insoluble displacing liquid. The hydrocarbon phase and the displacing liquid phase separate, forming a fluid interface between such phases under the initial static conditions. A sample of a porous material is placed within the closed fluid system. Thereafter both the hydrocarbon and displacing liquid phases are pumped into one end of the sample, whereby the sample becomes saturated. Changes in the level of the fluid interface within the closed system are measured in response to the flow rates of the two phases, such changes being representative of the fluid saturation condition with the sample of porous material.

The initial pumping rates for the two phases continue until an initial equilibrium condition is reached, the changes in the level of the fluid interface between the static condition and the initial equilibrium condition being representative of the saturation condition of the porous material at the specific pumping rates for the hydrocarbon and displacing liquid phases.

Upon an initial state of equilibrium being reached, one or more of the pumping rates may be changed and pumping continued until a second equilibrium state is reached, the change in the fluid interface level between the initial and second equilibrium states being representative of the saturation condition of the porous material between the initial and second fluid flow rates.

DESCRIPTION OF THE PREFERRED EMBODIMENT

Figure 1:
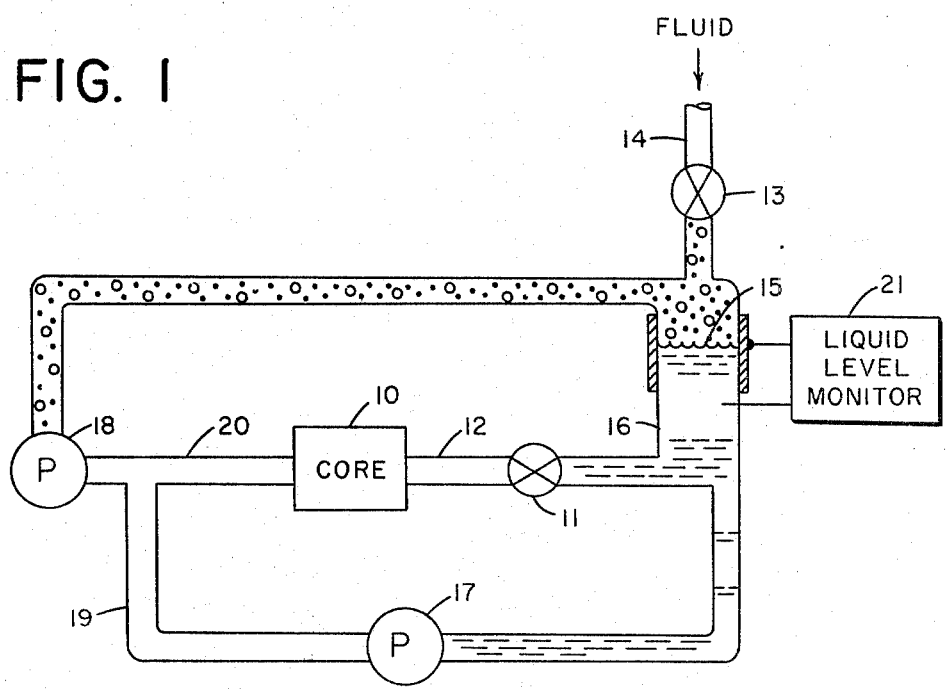
FIGS. 1 and 2 illustrate a closed fluid system for carrying out the saturation measurement of the present invention.

Referring now to FIG. 1, there is illustrated a preferred embodiment for carrying out the method of the present invention. A core sample 10, taken from a subterranean formation, and whose saturation characteristics are to be determined, is placed into a closed fluid system. To establish an initial fluid condition a valve 11 in flow line 12 is closed and a valve 13 in flow line 14 is opened. A liquid phase capable of displacing a hydrocarbon phase within a core sample, yet insoluble with such hydrocarbon, flows through line 14 and valve 13 until a desired fluid level 15 is reached by the filling of container or carrier member 16. The displacing liquid phase is prevented from impregnating the core 10 by the closed valve 11 and the pump 17 which is initially inoperable. Thereafter, the hydrocarbon phase is flowed through line 14 and valve 13 until the level of the hydrocarbon phase in the system reaches the valve 13. At this point the valve 13 is closed. The hydrocarbon phase is prevented from impregnating the core 10 by the pump 18 which is initially inoperable. The level 15 of the fluid interface between the hydrocarbon and displacing liquid phases is measured by the liquid level monitor 21 and the zero or static level condition.

To impregnate the core sample 10 with both the hydrocarbon and displacing liquid the valve 11 is opened and the pumps 17 and 18 simultaneously started. The displacing liquid phase from pump 17 passes through line 19 and mixes in line 20 with the hydrocarbon phase from the pump 18 to supply a multiphase liquid to core sample 10. As pumping continuous, this multiphase liquid passes into core 10 with one or both of the phases exiting from core sample 10 and passing through line 12 and valve 11 into the container member 16 where the hydrocarbon phase and displacing liquid phases separate at the interface 15. The level of interface 15 changes in response to the characteristics of the core sample 10. For example, the core sample 10, as taken from a subterranean formation may be saturated with the liquid hydrocarbon. A certain amount of this original liquid hydrocarbon in the core sample will be displaced by the impregnating multi-phase liquid and will flow through line 12 and valve 11 into container 16. Upon an equilibrium condition being reached within the core sample, the level of the interface 15 will again become static. The change in such level between the initial static condition and the equilibrium static condition is determined by the liquid level monitor 21 as being a measure of the volume of liquid hydrocarbon displaced within the core sample by the brine solution.

Upon reaching equilibrium with the initial pumping rates for the two fluid phases, it may be desirable to change one or both of such pumping rates until such time as a subsequent equilibrium condition is established for such new pumping rates. In this matter any change in the saturation conditions within the core sample may be measured for the new flow rate conditions. Particularly suitable ratios for pumping rates of the hydrocarbon phase to the displacing liquid may vary as follows: 10:1, 5:1, 1:1, 1:5 and 1:10. For example, with successively decreasing flow rate ratios for the hydrocarbon phase to displacing liquid, the level of interface 15 will lower indicating continued hydrocarbon displacement and increased displacing liquid saturation within the core sample. In the alternative, with successively increasing flow rate ratios, the level of interface 15 will increase, establishing an increasing displacing liquid saturation and the hysteresis effect. Eventually an equilibrium point will be reached where there will be no further change in saturation with changes in the flow rate ratio. In this manner significance may be attached to the measurement of the core sample characteristics for the various fluid flow phase conditions.

A particularly suitable use for the foregoing described saturation measurements is in the plotting of the saturation conditions at various fluid flow rates against core permeability. Such permeability can be measured simultaneously with saturation by monitoring the pressure drop across the core for the varying fluid flow rates. Permeability determinations from such pressure drop measurements may be carried out in accordance with the teachings of U.S. Pat. No. 2,867,116 to J. S. Aronofoky et al. In this manner it is possible to estimate the fluid saturation characteristics of an earth material forming the matrix of a subterranean hydrocarbon reservoir and to estimate the potential total production rate of production of hydrocarbons from the reservoir.

In most instances, the liquid hydrocarbon to be displaced from the core sample will be oil while the insoluble displacing liquid will be a typical water or surfactant flooding agent.

Figure 2:
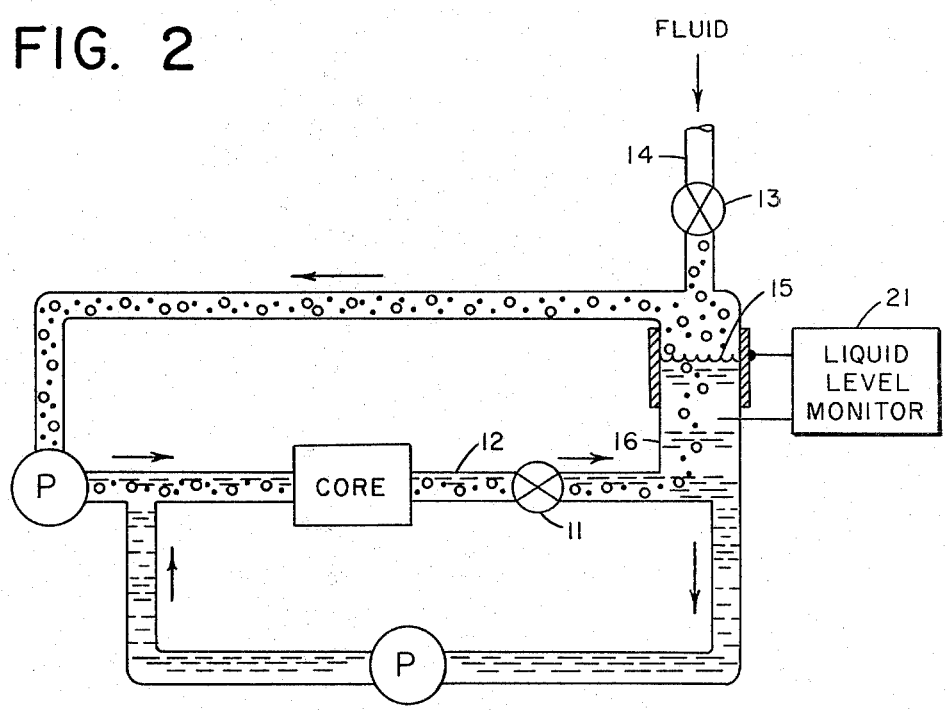
Figure 3:
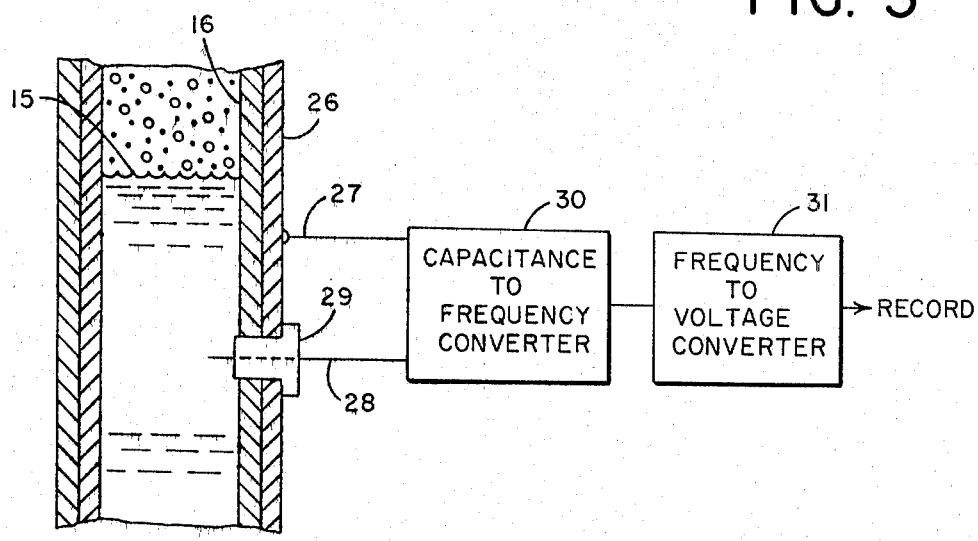
FIGS. 3 and 4 illustrate the liquid level monitor portion of the system of FIGS. 1 and 2.

Referring now to FIG. 3, there is illustrated the liquid level monitor of FIGS. 1 and 2. The displacing liquid whose level 15 is to be monitored, is mixed with a suitable substance to cause said liquid to become electrically conductive. Sodium-chloride, for example, may be mixed with a displacing water medium to provide an electrically conductive brine solution. The container or carrier 16 for the displacing liquid comprises a non-conductive material, such as glass. Surrounding carrier 16 is a conductive material or sheathing 26 such as aluminum foil. A first electrode 27 is affixed to the conductive material 26. A second electrode 28 passes through the conductive material 26 and container 16 and is positioned within the displacing liquid. This electrode 28 is insulated from the conductive material 27 by a suitable feedthrough connector 29. In this embodiment, the conductive displacing liquid and conductive material function as a pair of capacitance plates with the glass carrier functioning as the dielectric between such plates. Capacitance can be measured across connecting electrodes 27 and 28. By calibrating a measured capacitance with the level of the displacing liquid within the carrier, any change in such measured capacitance can be directly related to a change in fluid interface 15.

Electrodes 27 and 28 are connected to a capacitance-to-frequency converter 30, which in turn is applied to a frequency-to-voltage converter 31. The voltage output from converter 31 may be recorded as a direct measure of the level of the fluid interface 15 within the carrier 16 at any given point in time.

In measuring capacitance, a change in the displacing water layer changes the surface area of the water exposed to conductive material 11 in accordance with the following expression:

$$C_m = 2248 \, AK/t(10^{10}) \quad (1)$$

where, $C_m$ = measured capacitance (farads)
$A$ = liquid surface area between the capacitance plates (square inches)
$K$ = dielectric constant, and
$t$ = thickness of the dielectric carrier (inches).

The area $A$ is directly proportional to the liquid column height and the capacitance $C_m$ is directly proportional to area. Therefore, the capacitance $C$, as measured by the electrodes 27 and 28, changes linearly with changes in the fluid interface 15 within the carrier 16.

The capacitance-to-frequency converter changes the capacitance measurement into a square wave signal having a frequency inversely proportional to capacitance. This square wave signal is converted into a D.C. voltage by the frequency-to-voltage converter 31 and recorded. This D.C. voltage is linearly proportional to the measured capacitance and, therefore, to fluid interface level 15.

Figure 4:
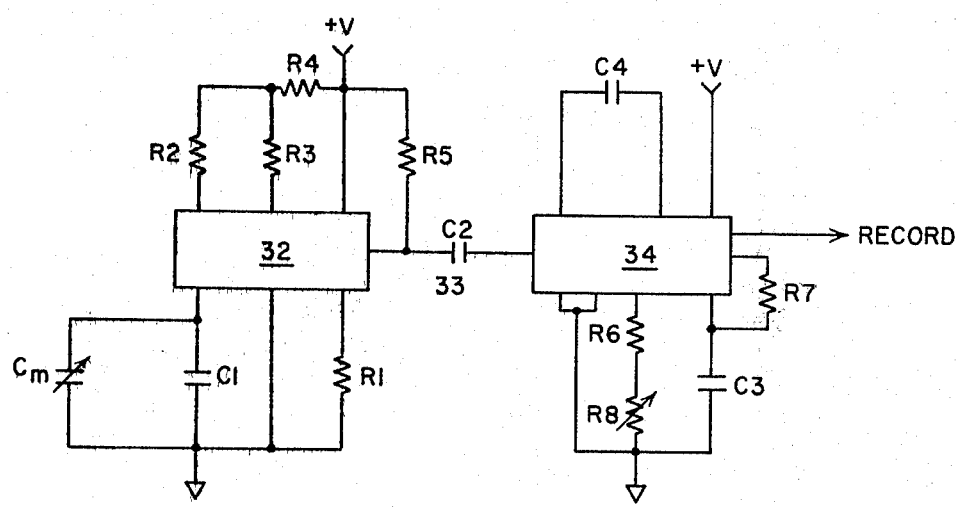

Referring now to FIG. 4, there is disclosed one embodiment for the circuitry of units 30–31. The capacitance-to-frequency conversion is accomplished by way of the converter 32. This converter employs an input capacitor C1 of about 2000 picofarads across which the variable capacitance to be measured $C_m$, is connected in parallel. Desired bias conditions are supplied by the resistors R1–R5. The frequency of the square wave output on line 33 is inversely proportional to the parallel combination of capacitor C1 and the measured capacitance of $C_m$.

Capacitor C2 couples the square wave signal from the capacitance-to-frequency converter 32 to the frequency-to-voltage converter 34. Desirable bias conditions are established for converter 34 by the resistors R6–R8 and capacitors C3 and C4. The D.C. voltage output from converter 34 may be applied to a suitable voltage recording means.

Having now described the liquid level monitor in conjunction with the circuitry of FIG. 4, it is to be understood that such circuitry is merely representative of one embodiment. In accordance with such embodiment, the following sets forth specific types of circuit components.

| Reference Designation | Description |
| --- | --- |
| +V | +15 VDC |
| Converter 32 | Texas Instruments 8038 |
| Converter 34 | Texas Instruments CD 4046B |
| Resistors R2 & R3 | 3 Kohms |
| Resistor R4 | 1 Kohm |
| Resistor R5 | 10 Kohms |
| Resistor R1 | 82 Kohms |
| Resistors R6 & R7 | 49.9 Kohms |
| Resistor R8 | 100 Kohms |
| Capacitor C1 | 2000 pf |
| Capacitors C2 & C4 | 1000 pf |
| Capacitor C3 | 10,000 pf |

While a particular embodiment of the present invention has been shown and described, other modifications are within the true spirit and scope of the invention. The appended claims are therefore, intended to cover such modifications.

What is claimed is:

1. A method for determining the characteristics of a porous material from a subterranean formation, comprising:

(a) establishing a closed fluid system of a multiphase fluid, one phase being a liquid hydrocarbon and another phase being an insoluble displacing liquid, said hydrocarbon phase and said displacing liquid phase separating and forming a fluid interface between said phases, (b) placing a sample of said porous material into said closed fluid system,
(c) detecting the level of said fluid interface under static conditions,
(d) pumping a portion of said hydrocarbon phase into a first end of said sample,
(e) pumping a portion of said displacing liquid phase into said first end of said sample, whereby said sample is saturated with said hydrocarbon phase and said displacing liquid phase and
(f) detecting a change in the level of said fluid interface in response to the flow of the hydrocarbon phase and displacing liquid phase through said sample, said fluid change being representative of the saturation characteristics of said porous material.

2. The method of claim 1 wherein said hydrocarbon phase is pumped into said sample at the same flow rate as said displacing liquid phase is pumped into said sample.

3. The method of claim 1 wherein said hydrocarbon phase is pumped into said sample at a different flow rate than said displacing liquid phase is pumped into said sample.

4. The method of claim 1 wherein the pumping of said hydrocarbon phase and said displacing liquid phase continues until an initial state of equilibrium is reached, the change in the level of said fluid interface between the static and initial equilibrium conditions being representative of the saturation condition of said sample at the specific pumping rates for said hydrocarbon phase and said displacing liquid phase.

5. The method of claim 1 wherein the initial pumping rates for at least one of said hydrocarbon or displacing liquid phase is changed to a second rate and pumping of both phases continued until a second equilibrium state is reached, the change in said fluid interface between said initial and second equilibrium conditions being representative of the change in saturation characteristics of said sample between said initial and second pumping rates.

* * * * *